Reissued Aug. 13, 1940 Re. 21,528

UNITED STATES PATENT OFFICE 21,528

AMINE HYDRIODIDES

Frank B. Fisk, Indianapolis, Ind., assignor, by mesne assignments, to Allied Laboratories, Inc., Kansas City, Mo., a corporation of Delaware No Drawing. Original No. 2,128,741, dated August 30, 1938, Serial No. 119,271, January 6, 1937. Application for reissue November 4, 1939, Serial No. 302,857

4 Claims. (Cl. 260—583)

This invention relates to iodine compounds suitable for use in internal medication.

The chief object of this invention is to produce an iodine compound which is not dangerous to produce, which is not dangerous in its use and which is stable to light and air.

The chief feature of the invention consists in amine hydriodides in pure form.

The administration of iodine in internal medication is well known. Alkali salts of hydriodic acid, such as sodium and potassium iodide, have been commonly used for internal medication. The salts are solid and in order to obtain the desired internal medication effect, large dosages are usually necessary. The material is usually given as tablets. The salts are objectionable because of their irritant action on the stomach. With the large dosages usually necessary, the salts may cause nausea and vomiting. In the absence of any better vehicle for supplying iodine for interal medication, the medical profession perforce has been restricted thereto unless hydriodic acid has been used.

Hydriodic acid, it is well known, appears to give better medication results than these salts. However, due to the fact that this acid will burn the mucous tissues if administered, the same must be diluted. This requires large dosages to secure the desired iodine medication effect. Usually when this liquid is used, it is administered as a syrup to minimize the burning effect before mentioned.

There has been prepared the hydriodides of ethylene diamine. Two forms have been produced, to-wit, the dihydriodide and the monohydriodide and either is satisfactory for the administration for internal medication purposes. Either or both may be safely prepared. Either or both are readily soluble each being a white crystal. Each is stable to light and air. Each contains an amount of iodine comparable to the amounts contained in the alkali iodides. Each of these products when administered, does not cause nausea or vomiting, does not burn the mucous tissues and may be readily added to various pharmaceutical combinations for synergistic effect in varying dosage. For example, either or both may be used in combination with alkaloids of the purine group, such as theobromine, with purine alkaloids and sedative drugs of the barbital type, such as pheno-barbital, with the salicylates, with or without vegetable drugs, or in combinations like the so-called mixed treatment formula for syphilis in which the new hydriodide would be treated with mercuric bichloride to give the corresponding soluble complex mercuric iodide.

The foregoing are set forth as examples of the use of either or both of these products. A number of other such possible combinations will readily suggest themselves to persons skilled in this art and such combinations are possible because these products contain iodine in inorganic combination and in amounts comparable to those found in the alkali salts and are readily soluble in water and other media. When administered directly in solution, their taste may be readily disguised. Briefly stated, therefore, either or both of these compounds possess all the desirable therapeutic features of hydriodic acid but are in solid form and avoid the administration of the free acid with its attendant disadvantages, and they possess the desirable therapeutic features of the alkali salts of hydriodic acid without the attendant irritant action on the stomach or the accompanying nausea and vomiting. Likewise, comparable to alkali salts of hydriodic acid they are entirely stable to light and air.

The two salts have these formulas:—

$NH_2CH_2CH_2NH_2.HI$ and $HI.NH_2CH_2CH_2NH_2.HI$

While both salts are quite satisfactory, as previously stated, as medicaments, the latter contains a somewhat greater proportion of iodine in the ratio of 81% as compared with 68%, and accordingly, is more desirable for the administration of iodine since smaller doses thereof will be required to produce a like iodine effect. From the formula before mentioned, it is apparent that one includes but one and the other includes two molecules of the acid.

The amine most suitable for forming such a salt or salts, is ethylene diamine.

A convenient method of preparing these salts by way of illustration only, is by mixing suitable molecular quantities of the concentrated aqueous solutions of ethylene diamine and hydriodic acid commercially available. Reaction occurs immediately. The desired salts will be readily obtained by concentrating the mixture on a water bath until crystallization takes place. The crystals are then filtered, washed thoroughly and then dried. The product is then usually pure enough for immediate use. If and when necessary, the product can be further purified by recrystallization from various solvents. A mixture of ethyl alcohol and water is especially suitable for this purpose.

The quantities of the reagents to be used may be calculated from their strengths, if known.

When their strengths are unknown, an indicator may be used to determine when the mixture has reached the proper degree of acidity. If, for instance, the mixture is neutral to metacresol purple or bromphenol blue, the product obtained on crystallization is the pure dihydriodide. If, however, the mixture is less acid, a mixture of the two salts, before mentioned, will be obtained, the proportion of monohydriodide increasing with decreasing acidity until finally when the acidity is suitable, the monohydriodide is obtained as pure crystals.

From the foregoing, therefore, it is evident that either salt may be obtained in pure form or any predetermined mixture of these salts may be obtained.

By way of illustration only, the following example of the preparation of the dihydriodide will now be given. To 45 lbs. of an aqueous solution of hydriodic acid (about 62.5%) was added gradually with stirring, 9 lbs. 2 oz. of an aqueous solution of ethylene diamine (about 70%). To this mixture was added the mother liquor from a previous similar lot. Titration of a sample of the mixture, using metacresol purple as an indicator, then showed 5 lbs. of hydriodic acid must be added to render the whole solution neutral to this indicator. When this amount of acid was added to the mixture, the same was heated on the water bath until a crystal crust over the surface of the solution or a pellicle was formed. The mixture was then cooled and allowed to crystallize. This resulted in the formation of relatively large size crystals. If the mixture is stirred during the cooling, the size of the crystals will be materially reduced. For tablet preparation, the latter procedure is preferred. The crystals were then removed by filtration, washed thoroughly with alcohol and dried. Analysis of a sample of the crystals showed the iodine content thereof to be 80.1%. The theoretically calculated content is 80.37%.

It is, of course, to be understood that the details of preparation may vary considerably without essentially altering the basic process. For instance, either or both of the reagents may be used in the pure state, since both are liquids, or they may be used in other than aqueous solutions—that is, in solutions which are not inimical to each other or to the resulting product or subsequent procedure.

Also, it is to be understood that concentration and crystallization may be accomplished by other procedure than that specified. Such a concentration and crystallization, for example, which is alternative in character, may be as by spraying the solution into a heated current of air. Any number of variations of the procedure hereinbefore specified by way of example, will readily suggest themselves to persons skilled in this art.

In addition to the hydriodides of ethylene diamine, before mentioned, there has been prepared and studied the hydriodides of monoethanolamine, diethanolamine and triethanolamine. These resemble very closely the salts of ethylene diamine in appearance, properties and method of preparation. Each of these bases is capable of forming one salt with hydriodic acid. Each of these salts is similarly effective medically and possesses the same advantages for iodine medication that the two first mentioned salts possess. However, their iodine content is markedly lower. Hence, a greater amount of these last mentioned salts must be used to provide iodine dosage equivalent to a given amount of either of the two first mentioned salts. These several salts each have the general formula $$(CH_2OHCH_2)_xNH_{(3-x)}.HI$$

where $x$ is an integer not greater than 3.

From these results, therefore, it is to be expected that amine hydriodides as a class will give similar excellent results in iodine medication. However, allowance must be made for the individual physiological action of the different amines used. For example, the gradual lowering of the blood pressure produced by ethylene diamine is frequently advantageous. Also the harmful physiological actions of some of the other amines might prevent their use in particular instances. The selection of ethylene diamine, monoethanolamine, diethanolamine and triethanolamine has been intentional, solely because each of the same is less toxic than other well known readily available amines.

With reference to the salts initially mentioned hereinbefore, it may be said that clinical results with a combination of theobromine, phenobarbital and ethylene diamine dihydriodide demonstrate that, by the use of this particular iodide, not only is satisfactory iodine action or medication secured without stomach irritation but the effect thereof is more prolonged than with the use of the ordinary alkali iodides so that the frequency and/or size of the doses (for example, tablets) may be diminished.

While the invention has been described in great detail in the foregoing specifications, the same is to be considered as illustrative and not restrictive in character. Various modifications of the method of preparation of the compounds prepared will readily suggest themselves to persons skilled in this art and the same as well as the modifications hereinbefore mentioned specifically, are all considered to be within the broad scope of the invention, reference being had to the appended claims.

The invention claimed is:

1. Ethylene diamine monohydriodide.
2. Ethylene diamine dihydriodide.
3. A mixture of ethylene diamine monohydriodide and ethylene diamine dihydriodide.
4. A hydriodide of ethylenediamine.

FRANK B. FISK.